US008871954B2

(12) United States Patent
Aduri et al.

(10) Patent No.: US 8,871,954 B2
(45) Date of Patent: Oct. 28, 2014

(54) PROCESS FOR THE PREPARATION OF ALDITOL ACETALS

(71) Applicant: Reliance Industries Limited, Maharashtra (IN)

(72) Inventors: Pavankumar Aduri, Maharashtra (IN); Parasu Veera Uppara, Maharashtra (IN)

(73) Assignee: Reliance Industries Limited, Mumbai (IN)

( * ) Notice: Subject to any disclaimer, the term of this patent is extended or adjusted under 35 U.S.C. 154(b) by 0 days.

(21) Appl. No.: 13/936,436

(22) Filed: Jul. 8, 2013

(65) Prior Publication Data

US 2013/0296581 A1    Nov. 7, 2013

Related U.S. Application Data

(63) Continuation of application No. PCT/IN2011/000123, filed on Feb. 28, 2011.

(30) Foreign Application Priority Data

Jan. 10, 2011 (IN) .............................. 81/MUM/2011

(51) Int. Cl.
*C07D 323/04* (2006.01)
*C07D 493/04* (2006.01)

(52) U.S. Cl.
CPC .................................. *C07D 493/04* (2013.01)
USPC ....................................................... 549/364

(58) Field of Classification Search
CPC .................................................... C07D 493/04
USPC ......................................................... 549/364
See application file for complete search history.

(56) References Cited

U.S. PATENT DOCUMENTS

| 3,721,682 | A | 3/1973 | Murai et al. |
| 4,267,110 | A | 5/1981 | Uchiyama |
| 4,429,140 | A | 1/1984 | Murai et al. |
| 4,562,265 | A | 12/1985 | Machell |
| 4,902,807 | A | 2/1990 | Kobayashi et al. |
| 5,023,354 | A | 6/1991 | Salome et al. |
| 5,104,840 | A | 4/1992 | Chauvin et al. |
| 5,731,474 | A | 3/1998 | Scrivens et al. |
| 5,892,124 | A * | 4/1999 | Olivier et al. ............. 568/324 |
| 6,500,964 | B2 | 12/2002 | Lever et al. |
| 6,527,977 | B2 | 3/2003 | Helber et al. |
| 6,573,405 | B1 | 6/2003 | Abbott et al. |
| 7,183,433 | B2 | 2/2007 | Abbott et al. |
| 7,196,221 | B2 * | 3/2007 | Abbott et al. ............. 564/282 |
| 2002/0137953 | A1 | 9/2002 | Lever et al. |
| 2005/0147889 | A1 | 7/2005 | Ohzuku et al. |
| 2006/0183654 | A1 | 8/2006 | Small |
| 2008/0221353 | A1 | 9/2008 | Tsunashima |
| 2008/0307703 | A1 | 12/2008 | Dietenberger et al. |
| 2009/0247432 | A1 | 10/2009 | Miller |
| 2013/0296580 | A1 | 11/2013 | Uppara et al. |

FOREIGN PATENT DOCUMENTS

| CN | 1858048 | 11/2006 |
| CN | 1903857 | 1/2007 |
| CN | 101440025 | 5/2009 |
| CN | 101544628 | 9/2009 |
| CN | 101723852 | 6/2010 |
| JP | 2009-057297 | 3/2009 |
| KR | 10-2008-0003855 | 1/2008 |
| WO | 00/41809 | 7/2000 |
| WO | WO02/26701 | 4/2002 |
| WO | 2006/007703 | 1/2006 |
| WO | WO2006/044187 | 4/2006 |
| WO | 2007/023814 | 3/2007 |
| WO | WO2012/095855 | 7/2012 |

OTHER PUBLICATIONS

International Search Report of PCT/IN2011/000123, dated Oct. 27, 2011, 3 pages.
Office Action and list of Accepted References for 13936393 to Uppara et al dated Oct. 10, 2013 17 pages.
International Search Report of PCT/IN2011/000120, dated Oct. 20, 2011, 3 pages.
Olivier-Bourbigou, H., et al., Applied Catalysis A: General, 373, 1-56, 2010, 56 pages.
Deetlefs, M., et al., Liquid Structure of the Ionic Liquid 1,3-Dimethylimidazolium Bis{(trifluoromethyl)sulfonyl}amide, J. Physical Chemistry B. 110, 12055-12061,2006, 7 pages.
Canongia Lopes, Jose N.A. and Agilio A. H. Padua, Nanostructural Organization in Ionic Liquids, J. Physical Chemistry B. 110, 3330-3335, 2006, 7 pages.
Wasserscheid, Peter and Wilhelm Keim, Angew. Chem. Int. Ed., Ionic Liquids—New "Solutions" for Transition Metal Catalysis, 2000, 39, 3772-3789, 18 pages.

* cited by examiner

*Primary Examiner* — Andrew D Kosar
*Assistant Examiner* — Raymond Covington
(74) *Attorney, Agent, or Firm* — Collard & Roe, P.C.

(57) ABSTRACT

The present invention is directed to a process for the preparation of 1,3:2,4-bis (4-methylbenzylidene) sorbitol (MDBS) and 1,3:2,4-bis (4-dimethylbenzylidene) sorbitol (DMDBS) by dehydrocondensating an aldehyde and an alditol using a hydrophobic ionic liquid as an acid catalyst. The ionic liquid used in the accordance with the process of the present invention is a phosphonium ion based ionic liquid.

13 Claims, No Drawings

US 8,871,954 B2

PROCESS FOR THE PREPARATION OF ALDITOL ACETALS

CROSS REFERENCE TO RELATED APPLICATIONS

This application is a continuation of PCT/IN2011/000123 filed on 28 Feb. 2011, which claims priority under 35 U.S.C. §119 of 81/MUM/2011 filed on 10 Jan. 2011, the disclosures of which are incorporated by reference. The international application under PCT article 21(2) was published in English.

FILED OF THE INVENTION

The present invention relates to a process for the preparation of 1,3:2,4-bis (4-methylbenzylidene) sorbitol (MDBS) and 1,3:2,4-bis (4-dimethylbenzylidene) sorbitol (DMDBS). Particularly, the present invention relates a process for preparation of MDBS and DMDBS using an ionic liquid.

BACKGROUND OF THE INVENTION

The acetal compound is the reaction product of an alditol and benzaldehyde. Alditol acetals, such as MDBS (1,3:2,4-bis (4-methylbenzylidene) sorbitol) and DMDBS (1,3:2,4-bis (4-dimethylbenzylidene) sorbitol) derivative compounds are known compounds which find their utility as an additive in polypropylene. Acetals of substituted and unsubstituted aldehydes are also known to be useful as nucleating agents, gelling agents, processing aids, and strength modifiers in polyolefin resins, polyester resins, deodorant, and antiperspirant compositions; hydrocarbon fuels and paints.

Acetal-alditols are typically prepared by the condensation reaction of an aromatic aldehyde with an alditol containing 6 carbon atoms like sorbitol. For MDBS and DMDBS structures, such reactions involve two moles of the aldehyde and one mole of an alditol.

Several methods for the preparation of acetal-alditols have been reported in U.S. Pat. Nos. 4,267,110, 3,721,682, 4,429, 140; 4,562,265; 4,902,807; 5,023,354; 5,731,474 and 6,500, 964.

The known processes suffer from several shortcomings. The known processes involve either the use of acidic catalysts or various organic solvents. Though mineral acids serve as good catalysts for the acetalization process, they do not come in contact with all the reactants due to limited solubility of the reactants. Furthermore, the final product resulting from such processes needs to be purified by neutralizing the residual free acid. Though the yields offered by all teachings are acceptable for the practical purposes, all the methods are not effective from the perspective of versatility, environmentally friendliness, energy efficient, reliability, cost-effective, and safe production.

The known processes also employ various organic solvents which necessitates high temperature for carrying out the reaction thereby increasing the cost component. Furthermore, most of solvents are very expensive and they too render the process un-economical. Still furthermore, the use of organic solvents also render these processes non-environment friendly.

Environmental force to minimize waste and re-use materials has prompted studies into "Green" chemistry. Solvents play very important role in chemical reactions; they serve to homogenize and mix reactants, and also act as a heat sink for exothermic processes. One of the biggest industrial concerns is substitute of volatile organic compounds (VOCs) particularly those that are toxic, such as $CH_2Cl_2$, and those that are hazardous to handle. Successful attempts to replace or limit the use of VOCs have been made in some cases, and these include processes that use no solvent or new solvent systems such as supercritical $H_2O$, supercritical $CO_2$, fluorous solvents, and recently ionic liquids (ILs).

Phosphonium ionic liquids have been widely employed for various chemical reactions/processes in recent years. Ionic liquids offer distinct advantages in reactions where water formation may hinder or inhibit the rate of reaction, if they are hydrophobic in nature. They are especially used as catalysts or as solvents in chemical reactions like Heck reactions, Suzuki cross-coupling reactions, Henry nitroaldol reaction, esterification, regio-selective hydroamination, hydrogenation, C&O-alkylation, and nitration with excellent conversions, selectivity and stability at high temperatures, and reusability. Similar such applications of the Phosphonium salt ionic liquids have been reported in WO 2006/007703, WO 0041809, U.S. Pat. No. 5,104,840, WO2007023814, JP2009057297, KR20080003855 and US2008221353.

None of the hitherto reported processes for preparation of MDBS and DMDBS have employed ionic liquids as catalysts and/or reaction medium. There exists a need for process for preparation of MDBS and DMDBS which uses ionic liquids as the catalyst and/or reaction medium. There also remains a need for a process for preparation of acetals, particularly MDBS and DMDBS which does not employ any expensive solvents or mineral acids.

OBJECTS OF THE INVENTION

It is an object of the present invention to provide a process for preparation of alditol acetal derivative compounds in high yields and purity.

It is another object of the present invention to provide a process that allows the preparation of symmetrical and asymmetrical dibenzylidene sorbitol compounds without any limitation.

It is still another object of the present invention to provide a process for preparation of acetal derivatives which is economical.

It is yet another object of the present invention to provide a process for preparation of acetal derivatives which is environment friendly.

It is yet another object of the present invention to provide a process for preparation of acetal derivatives which employs a single recyclable solvent.

It is yet another object of the present invention to provide a process for preparation of acetal derivatives wherein there the final product is devoid of any residual free acid.

It is yet another object of the present invention to provide a process for preparation of acetal derivatives which is safe.

It is a further object of the invention to provide a method which allows the production of monoacetal and diacetal derivatives without the formation of triacetal derivates.

SUMMARY OF THE INVENTION

Accordingly, in a first aspect of the present invention there is provided a process for preparation of acetal derivatives particularly, DMDBS and MDBS by dehydrocondensation reaction between an aldehyde and alditol which comprises the following steps:

dehydrocondensating an aldehyde and an alditol dissolved in a solvent by the addition of ionic liquid which acts as a catalyst under continuous stirring at a temperature of about 25° C. to about 80° C. to obtain a reaction mixture;

subjecting the reaction mixture to filtration to obtain a solid mass and a mother liquor containing the solvent and ionic liquid;

purifying the solid mass by washing and drying to obtain an acetal derivative without any free acid residue present therein.

In accordance with second aspect of the present invention, there is provided a process for preparation of acetal derivatives selected from the group consisting of DMDBS (1,3:2, 4-bis (3,4-dimethylbenzylidene) sorbitol) and MDBS (1,3:2, 4-bis (4-methylbenzylidene) sorbitol) comprising the following steps:

dehydrocondensating an aldehyde and an alditol dissolved in an ionic liquid under continuous stirring at a temperature of about 25° C. to about 80° C. to obtain a reaction mixture;

subjecting the reaction mixture to filtration to obtain a solid mass and a biphasic mixture of mother liquor and water;

removing water from the biphasic mixture to obtain the mother liquor; and purifying the solid mass by washing and drying to obtain an acetal derivative without any free acid residue present therein.

Typically, the aldehyde is selected from the group consisting of unsubstituted benzaldehyde, and substituted aldehydes including benzaldehyde, 4-methylbenzaldehyde, 3-methylbenzaldehyde, 4-propylbenzaldehyde, p-ethylbenzaldehyde, 4-butylbenzaldehyde, 4-Isopropylbenzaldehyde, 4-isobutylbenzaldehyde, 2,4-dimethylbenzaldehyde, 3,4-dimethylbenzaldehyde, 3,5-dimethylbenzaldehyde, 3-methyl-4-methoxybenzaldehyde, 2,4,5-trimethylbenzaldehyde, 3-hex-1-ynylbenzaldehyde, piperonal, 3-hydroxy-5,6,7,8-tetrahydro-2-naphthaldehyde, 3 -Methoxy-5,6,7,8-tetrahydro-2-naphthaldehyde, 3-Hydroxy-8-isopropyl-5-methyl-2-naphthaldehyde, 2-naphthaldehyde, 3-methoxybenzaldehyde, 4-methoxybenzaldehyde, 3,4-dimethoxybenzaldehyde, 3-ethoxybenzaldehyde, 4-ethoxybenzaldehyde, 3,4-diethoxybenzaldehyde, 4-allyloxybenzaldehyde, 4-propoxybenzaldehyde, 4-carboxybenzaldehyde, 3-bromobenzaldehyde, 4-bromobenzaldehyde, 2-chlorobenzaldehyde, 3-chlorobenzaldehyde, 4-chlorobenzaldehyde, 3-fluorobenzaldehyde, 4-fluorobenzaldehyde, 3,4-dichlorobenzaldehyde, 3,5-dichlorobenzaldehyde, 3,5-dibromobenzaldehyde, 3,5-difluorobenzaldehyde, 4-chloro-3-fluorobenzaldehyde, 3-bromo-4-fluorobenzaldehyde, 4-fluoro-3-methyl-, 5,6,7,8-tetrahydro-2-naphthaldehyde, 4-fluoro-3,5-dimethylbenzaldehyde, 4-(trifluoromethyl)benzaldehyde, 3-bromo-4-ethoxybenzaldehyde and mixtures thereof.

Typically, a hydrophobic ionic liquid is used wherein the cation providing source is selected from the group consisting of immidazolium, pyrazolium, triazolium, thiazolium, oxazolium, pyridinium, pyridazinium, pyrimidnium, pyrazinium, pyrrolidinium, quaterneray ammonium and phosphonium.

Preferably, a phosphonium ionic liquid is used. Typically, the phosphonium ionic liquid selected from the group consisting of Trihexyl (tetradecyl) phosphonium chloride and Trihexyl (tetradecyl) phosphonium bromide ionic liquids.

In accordance with one embodiment, the phosphonium ionic liquid is mixed in a solvent, said solvent is at least one selected from the group consisting of methanol, toluene, isopropyl alcohol, diethyl ether, tetrahydrofuran, dichloromethane, hexane.

Typically, the alditol is sorbitol (100%) or iso-propyl sorbitol. Alternatively, the alditol is an aqueous solution of sorbitol with a concentration in the range of about 40% to about 99%.

Typically, the method step of dehydocondensating is carried out at a temperature in the range of about 25° C. to about 80° C.

Typically, the stirring is continued for a period in the range of about 100° C. to about 800. Typically, the mother liquor is recycled in the method step of dehydrocondensating for at least 35 times, preferably 30 times.

DESCRIPTION OF THE INVENTION

In order to overcome the shortcomings of the hitherto reported processes which employ expensive solvents or mineral acid catalysts for the preparation of acetals, the inventors of the present invention have chosen the specific ionic liquids for the preparation of the acetals, particularly DMDBS and MDBS.

Accordingly, in a first aspect of the present invention there is provided a process for preparation of acetal derivatives particularly, DMDBS and MDBS by dehydrocondensation reaction between an aldehyde and alditol which comprises the following steps:

dehydrocondensating an aldehyde and an alditol dissolved in a solvent by the addition of a ionic liquid which acts as a catalyst under continuous stirring at a temperature of about 25° C. to about 80° C. to obtain a reaction mixture;

subjecting the reaction mixture to filtration to obtain a solid mass and a mother liquor containing the solvent and ionic liquid;

purifying the solid mass by washing and drying to obtain an acetal derivative without any free acid residue present therein.

The solvent used for dissolving the phosphonium ion in the process of the present invention is at least one selected from the group consisting of methanol, toluene, isopropyl alcohol, diethyl ether, tetrahydrofuran, dichloromethane, hexane. The use of a solvent along with the phosphonium ionic liquid, improves the yield and selectivity of the reaction.

In accordance with a second aspect of the present invention, there is provided a process for preparation of acetal derivatives selected from the group consisting of DMDBS (1,3:2,4-bis (3,4-dimethylbenzylidene) sorbitol) and MDBS (1,3:2,4-bis (4-methylbenzylidene) sorbitol) comprising the following steps:

dehydrocondensating an aldehyde and an alditol dissolved in an ionic liquid which acts as a catalyst and solvent under continuous stirring at a temperature of about 25° C. to about 80° C. to obtain a reaction mixture;

subjecting the reaction mixture to filtration to obtain a solid mass and a biphasic mixture of mother liquor and water;

removing water from the biphasic mixture to obtain the mother liquor; and purifying the solid mass by washing and drying to obtain an acetal derivative without any free acid residue present therein.

In accordance with a second aspect of the present invention, phosphonium ion liquid is used as such without the addition of a separate solvent as such. In such case, the phosphonium ion liquid serves the dual role of a catalyst as well as a medium for the dehydrocondensation reaction.

In accordance with the process of the present invention, a hydrophobic ionic liquid is used wherein the cation providing source is selected from the group consisting of immidazolium, pyrazolium, triazolium, thiazolium, oxazolium, pyridinium, pyridazinium, pyrimidnium, pyrazinium, pyrrolidinium, quaterneray ammonium and phosphonium.

Preferably, a phosphonium ionic liquid is used. Typically, the phosphonium ionic liquid is selected from the group consisting of Trihexyl (tetradecyl) phosphonium chloride and Trihexyl (tetradecyl) phosphonium bromide ionic liquids.

The aldehyde is typically selected from the group consisting of unsubstituted benzaldehyde, and substituted aldehydes including benzaldehyde, 4-methylbenzaldehyde, 3-methylbenzaldehyde, 4-propylbenzaldehyde, p-ethylbenzaldehyde, 4-butylbenzaldehyde, 4-lsopropylbenzaldehyde, 4-isobutylbenzaldehyde, 2,4-dimethylbenzaldehyde, 3,4-dimethylbenzaldehyde, 3,5-dimethylbenzaldehyde, 3-methyl-4-methoxybenzaldehyde, 2,4,5-trimethylbenzaldehyde, 3-hex-1-ynylbenzaldehyde, piperonal, 3-hydroxy-5,6,7,8-tetrahydro-2-naphthaldehyde, 3-Methoxy-5,6,7,8-tetrahydro-2-naphthaldehyde, 3-Hydroxy-8-isopropyl-5-methyl-2-naphthaldehyde, 2-naphthaldehyde, 3-methoxybenzaldehyde, 4-methoxybenzaldehyde, 3,4-dimethoxybenzaldehyde, 3-ethoxybenzaldehyde, 4-ethoxybenzaldehyde, 3,4-diethoxybenzaldehyde, 4-allyloxybenzaldehyde, 4-propoxybenzaldehyde, 4-carboxybenzaldehyde, 3-bromobenzaldehyde, 4-bromobenzaldehyde, 2-chlorobenzaldehyde, 3-chlorobenzaldehyde, 4-chlorobenzaldehyde, 3-fluorobenzaldehyde, 4-fluorobenzaldehyde, 3,4-dichlorobenzaldehyde, 3,5-dichlorobenzaldehyde, 3,5-dibromobenzaldehyde, 3,5-difluorobenzaldehyde, 4-chloro-3-fluorobenzaldehyde, 3-bromo-4-fluorobenzaldehyde, 4-fluoro-3-methyl-, 5,6,7,8-tetrahydro-2-naphthaldehyde, 4-fluoro-3,5-dimethylbenzaldehyde, 4-(trifluoromethyl)benzaldehyde, 3-bromo-4-ethoxybenzaldehyde while the alditol is typically sorbitol or iso-propyl sorbitol. In accordance with one of the embodiments, of the present invention sorbitol (100%) is used. In accordance with another embodiment of the present invention an aqueous solution of sorbitol with a concentration in the range of about 40% to about 99% is used as the alditol The dehydrocondensation reaction in accordance with the process of the present invention is carried out at a temperature in the range of about 25 to about 80° C. at atmospheric pressure. Typically, the stirring is carried out in a mechanical stirrer at a speed ranging between 100 to 800 rpm, preferably 350 rpm for a period of about 5 to about 10 hours.

In accordance with the one embodiment of the process of the present invention, the mother liquor is recycled in the method step of dehydrocondensating. In one embodiment, the mother liquor comprises the ionic liquid along with mono-intermediates of MDBS and DMDBS and unconverted raw material. In accordance with another embodiment of the present invention, mother liquor comprises ionic liquid, mono intermediates of MDBS, DMDBS and unconverted raw materials and a solvent. The recycling of the recovered ionic liquid therefore minimizes the consumption of aldehyde, solvent, and the ionic liquid.

Typically, the mother liquor is recycled in the dehydrocondensation reaction. The inventors of the present invention have found that the mother liquor can be recycled for 35 times without any loss in the catalytic activity of the ionic liquid present in the mother liquor. Preferably, the mother liquor obtained in the process of the present invention is recycled in the dehydrocondensation reaction for 30 times.

Separation of the products DMDBS or MDBS is easy from phosphonium ionic liquids as the solid product formed precipitates out at low temperatures. The aldol-acetal product obtained by the process of the present invention does not carry any acidic residue and unlike the known process there does not remain any need for neutralization of the reaction mixture after the completion of the dehydrocondensation reaction. In case of the prior art processes for the production of MDBS and DMDBS from aldehydes (4-methylbenzaldehyde and 3,4-dimethylbenzaldehyde) and sorbitol, it has been ascertained that in a single pass operation, the product is neutralized along with reaction mixture with caustic. This results in the loss of mono product and un-reacted 0-12 wt % aldehyde and the catalyst in the resultant mother liquor. This is particularly avoided in case of the process of the present invention wherein the loss of reactants and catalyst on account of the additional of the alkali during neutralization is circumvented by obviating the step of neutralization altogether thereby rendering the present process more cost-effective.

This clearly demonstrates the utility of the phosphonium ionic liquids in the preparation of the acetal-alditol compounds from the perspective of versatility, environmentally friendliness, reliability, cost-effectiveness, and safety.

The following examples further illustrate the present invention but are not to be construed as limiting the invention as defined in the claims appended hereto.

EXAMPLE—1

A 500 ml four necked round bottom flask equipped with a Dean-stark trap, condenser, thermometer, and a mechanical stirrer was charged with 130 ml of cyclohexane, 1.5 gms of Trihexyl (tetradecyl) phosphonium chloride ionic liquid as a catalyst and 8.5 ml of 3,4-dimethylbenzaldehyde.

To the well stirred hot reaction mixture (65° C.), a solution of 5 gms of sorbitol dissolved in 60 ml methanol was added over a period of 30 minutes. The reaction was stirred and heated under reflux for six hours. The reaction mixture was stirred at 350 rpm and the torque monitored constantly. The azeotrope was removed continuously and reaction vessel was replenished with fresh solvent. After five and half hours, reaction mixture was cooled. The product was filtered under vacuum to remove mother liquor containing methanol, unreacted 3,4-dimethyl benzaldehyde, mono intermediate of DMBDS and catalyst. The product was washed with methanol (250 ml), filtered and dried over night in a vacuum oven at 100° C. Yield and purity of the DMDBS obtained were 75% and 99% respectively.

EXAMPLE—2

The procedure of example 1 was repeated except, the reaction was carried out with mother liquor (filtrate) obtained from example 1. The mother liquor was replenished with reactants and solvents. Yield and purity were 72% and 99% respectively.

EXAMPLE—3

The procedure of example 1 is followed except, the reaction was carried out with 1.5 gms of Trihexyl (tetradecyl) phosphonium bromide ionic liquid as catalyst. Yield and purity were 39% and 99% respectively.

EXAMPLE—4 (COMPARATIVE EXAMPLE)

A 500 ml four necked round bottom flask equipped with a Dean-stark trap, condenser, thermometer, and a mechanical stirrer was charged with 130 ml of cyclohexane, 0.5 gms of para toluenesulfonic acid as a catalyst and 15.5 ml of 3, 4-dimethylbenzaldehyde . To the well stirred hot reaction mixture (65° C.), a solution of 10 gms of sorbitol dissolved in 60 ml methanol was added over a period of 30 minutes. The reaction is stirred and heated under reflux for six hours. The reaction mixture is stirred at 350 rpm and the torque monitored constantly. The azeotrope was removed continuously and reaction vessel is replenished with fresh solvent. After six hours, reaction mixture was cooled, neutralized with sodium hydroxide. The product was filtered under vacuum to remove mother liquor containing methanol, cyclohexane, unreacted 3,4-dimethyl benzaldehyde, mono intermediate of DMBDS. The product was washed with hot water (65° C.) (2×200 ml) and filtered. The product is finally washed with methanol (500 ml), filtered and dried over night in a vacuum oven at 100° C. DMDBS was obtained with purity of 99.5% and 90%-95% yield.

From the comparison of example 1 and the above example, it was confirmed that that phosphonium ionic liquids are capable of carrying out the said dehydration reaction as a catalyst employing a single solvent and the resulting product does not necessitate neturalization of the reaction mixture after the dehydrocondensation reaction.

EXAMPLE—5

The dehydration reaction of 3,4-dimethyl benzaldehyde and sorbitol was carried out with Trihexyl (tetradecyl) phosphonium chloride ionic liquid as solvent and catalyst. 3 gms of ionic liquid was take in 100 ml of round bottom flask and 3,4-dimethyl benzaldehyde (1.7 ml) and sorbitol (1 gm) are added to the ionic liquid and heated the flask contents to 80° C. and reaction was carried out for 10 hours. The flask contents were cooled and the product was filtered under vacuum and washed with methanol. The yield and purity are 67% and 97.5% respectively.

EXAMPLE—6

The procedure of example 5 was repeated with mother liquor (filtrate) obtained from the example 5. The mother liquor obtained was replenished with reactants and reaction was carried at 80° C. for 10 hrs. The yield and purity were 58% and 98% respectively.

EXAMPLE—7

The dehydration reaction of 3,4-dimethyl benzaldehyde (1.5 ml) and sorbitol (1 gm) was carried out with Trihexyl (tetradecyl) phosphonium chloride ionic liquid as a catalyst at 26° C. 3 gms of ionic liquid was added to 30 ml of methanol in 100 ml round bottom flask. 3,4-dimethyl benzaldehyde and sorbitol were added to the flask and reaction was carried out at 26° C. for 8 hours by stirring the contents. After 8 hrs the reaction was stopped and the solid product is filtered under vacuum and washed with methanol. The yield and purity were 80% and 99% respectively.

EXAMPLE—8

The procedure of example 7 was repeated with mother liquor obtained from example 7. The mother liquor obtained was replenished with reactants and methanol. The yield and purity were 99% and 99.2%.

EXAMPLE—9

The procedure of example 7 was repeated except that; Trihexyl (tetradecyl) phosphonium bromide ionic liquid was used as catalyst at 26° C. The yield and purity were 75% and 99%.

EXAMPLE—10

The procedure of example 7 was repeated except, 3,4-dimethyl benzadehyde was replaced with 4-methyl benzaldehyde. 1.25 gms of ionic liquid was added to 40 ml of methanol in 100 ml round bottom flask. 1.3 ml of 4-methyl benzaldehyde and 1 gms of sorbitol were added to the flask and reaction was carried at 26° C. for 8 hrs under stirring conditions. The solid product, MDBS was filtered under vacuum and washed with methanol. The yield and purity were 70% and 99% respectively.

EXAMPLE—11

The procedure of example 10 was repeated with mother liquor obtained from example 10. The mother liquor obtained was replenished with reactants and methanol. The yield and purity were 65% and 99%.

EXAMPLE—12

The procedure of example 10 was repeated except, Trihexyl (tetradecyl) phosphonium bromide ionic liquid was used as catalyst at 26° C. . The yield and purity were 22% and 93%.

While certain embodiments of the inventions have been described, these embodiments have been presented by way of example only, and are not intended to limit the scope of the inventions. Variations or modifications to the design and construction of this invention, within the scope of the invention, may occur to those skilled in the art upon reviewing the disclosure herein. Such variations or modifications are well within the spirit of this invention. The accompanying claims and their equivalents are intended to cover such forms or modifications as would fall within the scope and spirit of the invention.

The numerical values given for various physical parameters, dimensions and quantities are only approximate values and it is envisaged that the values higher than the numerical value assigned to the physical parameters, dimensions and quantities fall within the scope of the invention and the claims unless there is a statement in the specification to the contrary.

The invention claimed is:

1. A process for preparation of acetal derivatives particularly, DMDBS (1,3:2,4-bis (3,4-dimethylbenzylidene) sorbitol) and MDBS (1,3:2,4-bis (4-methylbenzylidene) sorbitol) by dehydrocondensation reaction between an aldehyde and alditol which comprises the following steps:
dehydrocondensating an aldehyde and an alditol dissolved in a solvent by the addition of ionic liquid which acts as a catalyst under continuous stirring at a temperature of about 25° C. to about 80° C. to obtain a reaction mixture;
subjecting the reaction mixture to filtration to obtain a solid mass and a mother liquor containing the solvent and ionic liquid; and
purifying the solid mass by washing and drying to obtain an acetal derivative without any free acid residue present therein.

2. The process for preparation of acetal derivatives selected from the group consisting of DMDBS (1,3:2,4-bis (3,4-dimethylbenzylidene) sorbitol) and MDBS (1,3:2,4-bis (4-methylbenzylidene) sorbitol) comprising the following steps:
dehydrocondensating an aldehyde and an alditol dissolved in an ionic liquid which acts as a catalyst under continuous stirring at a temperature of about 25° C. to about 80° C. to obtain a reaction mixture;

subjecting the reaction mixture to filtration to obtain a solid mass and a biphasic mixture of mother liquor and water;

removing water from the biphasic mixture to obtain the mother liquor; and purifying the solid mass by washing and drying to obtain an acetal derivative without any free acid residue present therein.

3. The process as claimed in claim 1, wherein the ionic liquid acts as an acid catalyst.

4. The process as claimed in claim 1, wherein the solvent is at least one solvent selected from the group consisting of methanol, toluene, isopropyl alcohol, diethyl ether, tetrahydrofuran, dichloromethane and hexane.

5. The process as claimed in claim 2, wherein the ionic liquid acts as an acid catalyst as well as a medium.

6. The process as claimed in claim 1, wherein the aldehyde is selected from the group consisting of unsubstituted benzaldehyde, and substituted aldehydes benzaldehyde, 4-methylbenzaldehyde, 3-methylbenzaldehyde, 4-propylbenzaldehyde, pethylbenzaldehyde, 4-butylbenzaldehyde, 4-lsopropylbenzaldehyde, 4 isobutylbenzaldehyde, 2,4-dimethylbenzaldehyde, 3,4-dimethylbenzaldehyde, 3,5-dimethylbenzaldehyde, 3-methyl-4-methoxybenzaldehyde, 2,4,5-trimethylbenzaldehyde, 3-hex-1-ynylbenzaldehyde, piperonal, 3-hydroxy-5,6,7,8-tetrahydro-2-naphthaldehyde, 3-Methoxy-5,6,7,8-tetrahydro-2-naphthaldehyde, 3-Hydroxy-8-isopropyl-5-methyl-2-naphthaldehyde, 2-naphthaldehyde, 3-methoxybenzaldehyde, 4-methoxybenzaldehyde, 3,4-dimethoxybenzaldehyde, 3-ethoxybenzaldehyde, 4-ethoxybenzaldehyde, 3,4-diethoxybenzaldehyde, 4-allyloxybenzaldehyde, 4-Propoxybenzaldehyde, 4-carboxybenzaldehyde, 3-bromobenzaldehyde, 4-bromobenzaldehyde, 2-chlorobenzaldehyde, 3-chlorobenzaldehyde, 4-chlorobenzaldehyde, 3-fluorobenzaldehyde, 4-fluorobenzaldehyde, 3,4-dichlorobenzaldehyde, 3,5-dichlorobenzaldehyde, 3,5-dibromobenzaldehyde, 3,5-difluorobenzaldehyde, 4-chloro-3-fluorobenzaldehyde, 3-bromo-4-fluorobenzaldehyde, 4-fluoro-3-methyl-, 5,6,7,8-tetrahydro-2-naphthaldehyde, 4-fluoro- 3,5-dimethylbenzaldehyde, 4-(trifluoromethyl)benzaldehyde, 3-bromo-4-ethoxybenzaldehyde and mixtures thereof.

7. The process as claimed in claim 1, where in the ionic liquid is a hydrophobic ionic liquid selected from the group consisting of Trihexyl (tetradecyl) phosphonium chloride and Trihexyl (tetradecyl) phosphonium bromide ionic liquids.

8. The process as claimed in claim 1, wherein the alditol is selected from the group consisting of iso-propyl sorbitol, and sorbitol.

9. The process as claimed in claim 1, wherein the alditol is an aqueous solution of sorbitol with a concentration in the range of about 40% to about 99%.

10. The process as claimed in claim 1, wherein the dehydocondensating step is carried out at a temperature in the range of about 25° C. to about 80° C.

11. The process as claimed in claim 1, wherein the stirring rate is in the range of about 100 to about 800 rpm.

12. The process as claimed in claim 1, wherein the mother liquor is recycled in the dehydrocondensating step at least 35 times.

13. The process as claimed in claim 1, wherein the mother liquor is recycled in the dehydrocondensating step at least 30 times.

* * * * *